United States Patent [19]

Prather

[11] Patent Number: 5,172,192
[45] Date of Patent: Dec. 15, 1992

[54] IN-SITU SPECTROPHOTOMETRIC PROBE

[76] Inventor: William S. Prather, 2419 Dickey Rd., Augusta, Ga. 30906

[21] Appl. No.: 478,328

[22] Filed: Feb. 12, 1990

[51] Int. Cl.⁵ .............................................. G01N 21/00
[52] U.S. Cl. ..................................... 356/440; 356/436
[58] Field of Search ............... 356/300, 410, 436, 440, 356/409, 39, 412; 250/576, 227.23, 227

[56] References Cited

U.S. PATENT DOCUMENTS

| | | | |
|---|---|---|---|
| 1,939,088 | 12/1933 | Styer | 356/436 |
| 3,785,734 | 1/1974 | Walters et al. | 356/36 |
| 4,369,364 | 1/1983 | Kuntermann | 250/227 |
| 4,591,268 | 5/1986 | Lew | 356/338 |
| 4,628,872 | 12/1971 | Miranda | 356/201 |
| 4,678,326 | 1/1983 | Kuntermann | 250/227 |
| 4,747,959 | 5/1988 | Ho et al. | 210/768 |
| 4,786,171 | 11/1988 | LeFrebre et al. | 356/436 |
| 4,907,037 | 3/1990 | Boisde et al. | 356/412 |
| 4,917,491 | 7/1988 | Ring et al. | 356/440 |

Primary Examiner—F. L. Evans
Assistant Examiner—K. P. Hantis
Attorney, Agent, or Firm—Harold M. Dixon; William R. Moser; Richard E. Constant

[57] ABSTRACT

A spectrophotometric probe for in situ absorption spectra measurements comprising a first optical fiber carrying light from a remote light source, a second optical fiber carrying light to a remote spectrophotometer, the proximal ends of the first and second optical fibers parallel and coterminal, a planoconvex lens to collimate light from the first optical fiber, a reflecting grid positioned a short distance from the lens to reflect the collimated light back to the lens for focussing on the second optical fiber. The lens is positioned with the convex side toward the optical fibers. A substrate for absorbing analyte or an analyte and reagent mixture may be positioned between the lens and the reflecting grid.

1 Claim, 2 Drawing Sheets

IN-SITU SPECTROPHOTOMETRIC PROBE

BACKGROUND OF THE INVENTION

1. Field of the Invention and Contract Statement

The present invention relates to an apparatus for spectrophotometric measurement of concentrations of chemical substances. The United States Government has rights in this invention pursuant to Contract No. DE-AC09-76SR00001 between the U.S. Department of Energy and E. I. DuPont de Nemours & Co.

2. Discussion of Background

Measurements of the concentrations of chemical substances found in industrial process streams, groundwater and other sources must be accurate and precise. Sometimes these substances are present in minute but significant concentrations. Although spectrophotometric absorption can be both an accurate and precise technique for measuring chemical concentrations, it has not been practical for in situ use. Spectrophotometry heretofore required a referenced light source and the ability to "see" through samples that could be very murky.

Referencing can sometimes be very difficult or impossible. It may be impossible to remove a chemical substance from its environment or to control the source or sources of light. Because spectrophotometry is capable of very precise measurements when properly referenced, making assumptions about the spectrum of a light source that cannot be referenced severely qualifies otherwise precise results.

In a companion patent application, Ser. No. 478,327, filed on Feb. 12, 1990, now U.S. Pat. No. 5,039,224, the inventors of the present apparatus have claimed a method for self-referencing spectrophotometry. The description of that method is incorporated herein by reference and the apparatus of the present invention preferably makes use of that method. That method, in some circumstances, involves use of a reagent to be mixed with the analyte to facilitate self-referencing.

"Seeing" through some chemical substances can be difficult. In measurements of groundwater contamination or chemical substances found in other environments, some compounds are so colored that light does not pass through more than a fraction of an inch of material. If the solution bearing the chemical substance also bears particulate matter, it is especially challenging to obtain enough light for a spectrophotometric measurement.

When a light source and a spectrophotometer must be moved closer to each other to reduce the amount of material through which the light must pass, it is sometimes necessary to use a pump to overcome the drop in fluid pressure that occurs between them.

SUMMARY OF THE INVENTION

An object of the invention is to provide a probe for making spectrophotometric measurements.

Another object of the invention is to provide a probe for in situ spectrophotometric measurements of chemical substances in industrial process streams, groundwater and the like.

To achieve the foregoing and other objects and in accordance with the purpose of the invention, as embodied and broadly described herein, the invention comprises a first and second optical fiber for carrying light from a remote light source to the probe and from the probe to a spectrophotometer, respectively, the ends of which optical fibers are adjacent and coterminal, a planoconvex lens to collimate light from the first optical fiber and focus light on the second optical fiber, a porous reflector, such as a reflecting grid, spaced a small distance from the lens, with the analyte therebetween, to reflect collimated light from the first optical fiber back to the lens for focussing on the second optical fiber.

In an alternative embodiment, an optically transparent, non-biodegradable substrate may be placed between the porous reflector and the lens, or combined with the reflector, for absorbing a photoreactive chemical substance. If the chemical substance is not photoreactive, the substrate can be coated with a reagent. When the apparatus with substrate is placed in the chemical substance, the reagent will mix with the substance to form a mixture having different photoreactive properties than the reagent or substance alone.

Several absorption spectra are taken short time intervals apart, each succeeding spectra altered from the first by the photochemical effect of the light of the previous measurement on the analyte, or by the reagent-analyte complex. The difference in the spectra correlates with the concentration of the analyte. Using a reagent-analyte complex of known photolytic properties, a known exposure time, a known delay time and measuring a known analyte, the concentration of the analyte can be immediately derived from the spectra.

The apparatus can be positioned in an industrial process stream, in groundwater, in well water or in other environments for spectrophotometric measurements taken over an extended period of time to determine changes in concentration, thus obviating the need for periodic sample gathering.

Reference is now made in detail to the present preferred embodiment of the invention, an example of which is given in the accompanying drawings.

A BRIEF DESCRIPTION OF THE DRAWINGS

The accompanying drawings, which are incorporated in and form a part of the specification, illustrate the invention and, together with the description, serve to explain the principles of the invention. In the drawings.

DETAILED DESCRIPTION OF THE INVENTION

The present invention is a probe for measuring the concentration of an analyte, a chemical substance of interest, by spectrophotometry. Preferably, the probe uses the photoreactive properties of certain chemical substances for self-referencing, as described in the companion patent application noted above.

Figure 1:
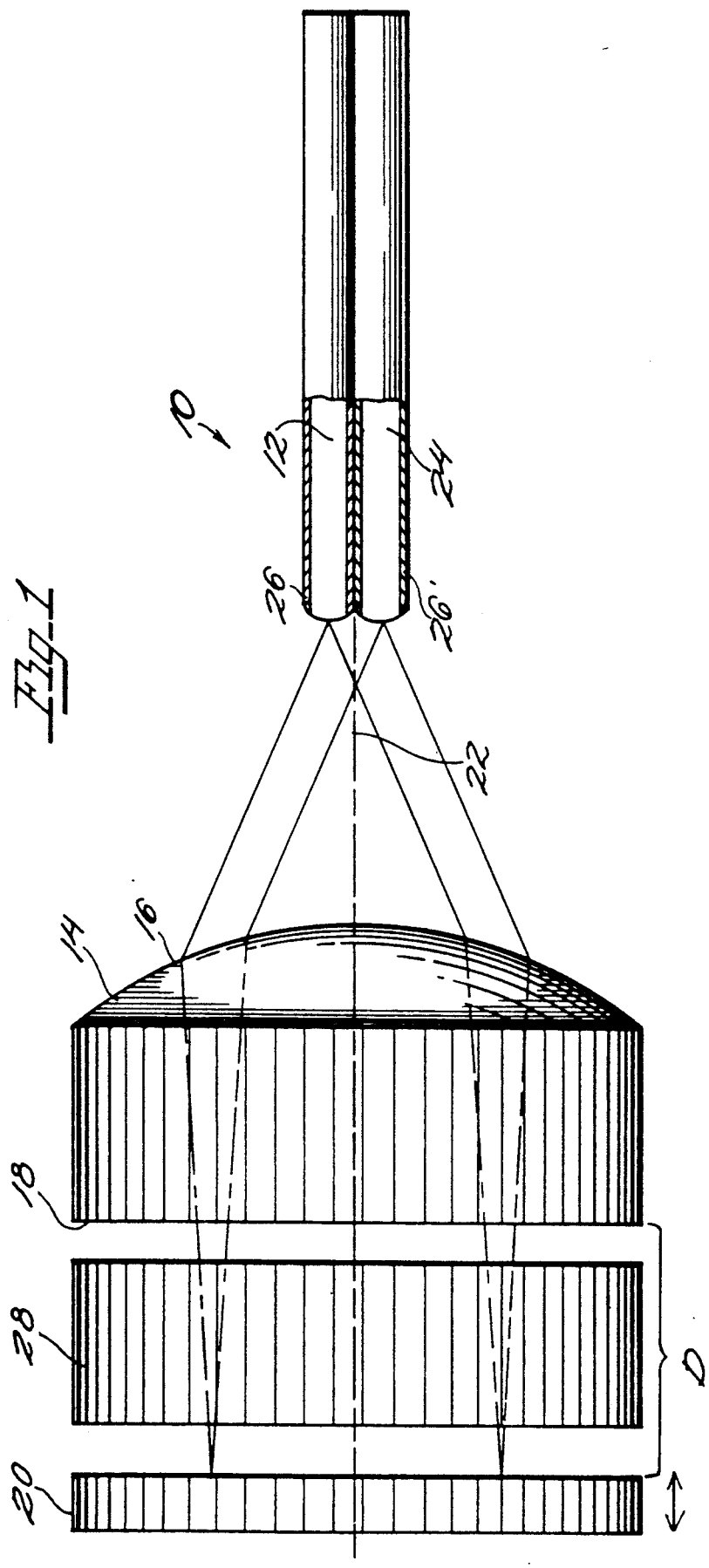
FIG. 1 is a side, partial cross-sectional view of the present invention.
Figure 2:
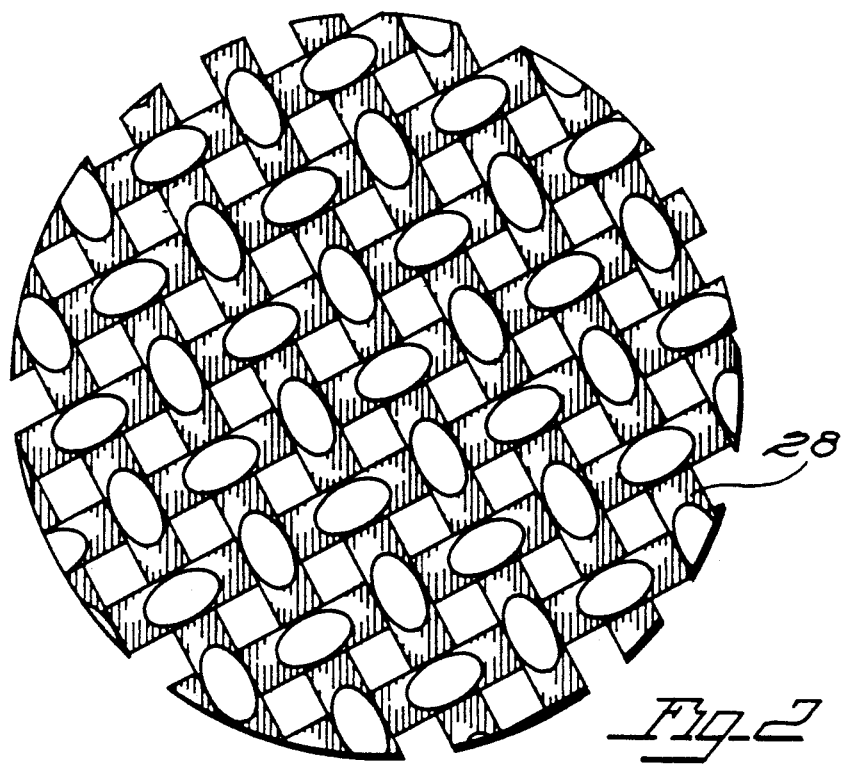
FIG. 2 is an end view of the porous reflector, in this case a grid, according to the present invention.

Referring now to FIG. 1, which shows a partial cross sectional, side view of the probe 10, light from a remote light source (not shown) is carried by a first optical fiber 12. The light then passes through a planoconvex lens 14 having its convex side 16 toward the first optical fiber 12 so that the light is collimated and directed from a plane side 18 of lens 14 toward a porous reflector reflecting grid 20. Reflector 20 is moved a short distance "d" from lens 14, typically about 50 micrometers, the distance depending in the main on the brightness of the light source, the reflectivity of the reflector, and the relative opacity of the analyte. Lens 14 is oriented with its convex side 16 toward first optical fiber 12 and its plane side 18 toward reflecting grid 20 to decouple the index of refraction of lens 14 from that of the analyte which may be changing due to changing concentration of the analyte. In a preferred embodiment, lens 14 is made of fused silica and reflector 20 is made of polished metal screen, as shown in FIG. 2.

First optical fiber 12 is positioned just off the optical axis 22 of lens 14 so that the collimated light strikes reflector 20 at a slight angle from normal incidence. The light is reflected back to lens 14 where it is focused on a second optical fiber 24, also located just off optical axis 22 parallel and coterminal with first optical fiber 12. Focused light is then carried to a remote spectrophotometer (not shown).

Both first and second optical fibers are carried within a buffer 26 and 26' and are preferably parallel and coterminus for compactness and for maintaining proper alignment with respect to each other and lens 14.

In an alternative embodiment, an optically transparent, non biodegradable substrate 28, preferably made of plastic, is placed between reflector 20 and lens 14. Most preferably, a porous substrate 30 having a porous reflective backing 32 as shown in FIG. 3a, or a diffusely reflective porous substrate 34 as shown in FIG. 3b, can be used in lieu of reflector 20 and substrate 28.

Figures 3A, 3B, 3C:
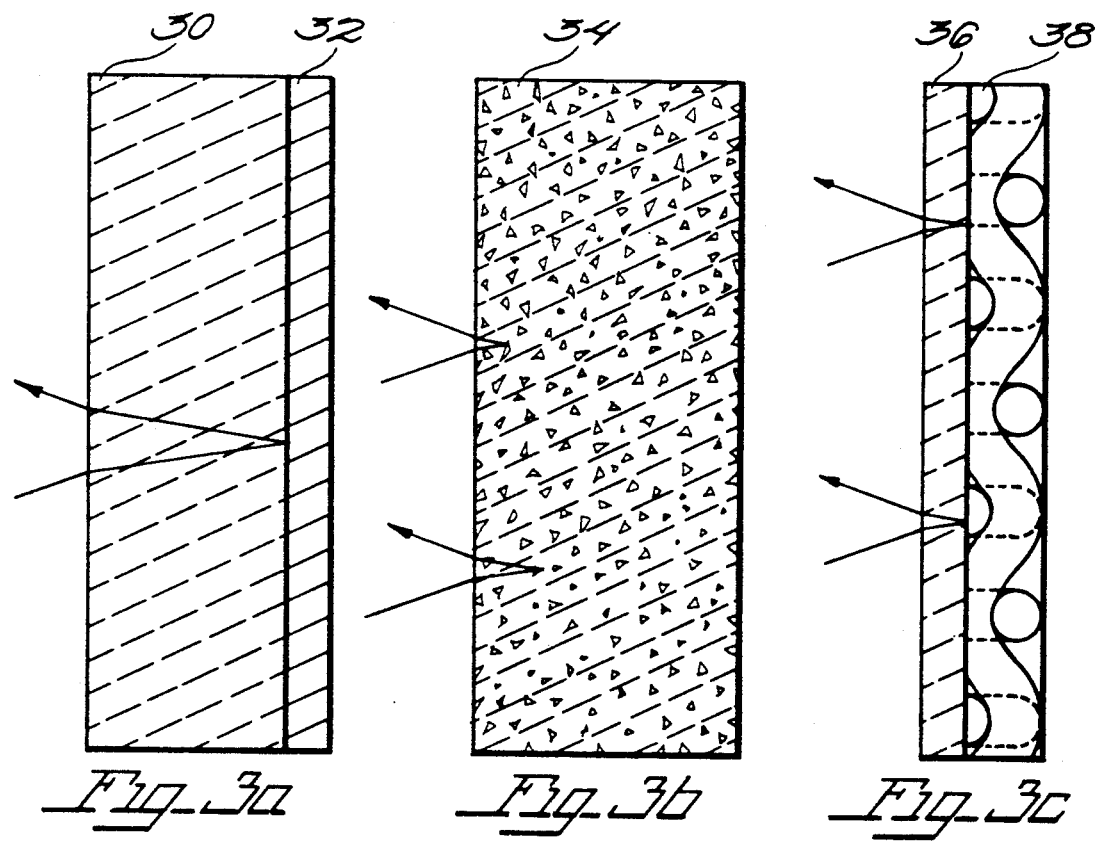
FIGS. 3a, 3b and 3c are cross sectional views of alternative embodiments of the porous substrate according to the present invention.

In another embodiment, shown in FIG. 3c, reflector 20 and substrate 28 are replaced by a porous membrane 36 stretched over a polished metal grid backing 38. It is important that reflector 20 and substrate 28, or their alternative embodiments in FIGS. 3a, 3b, 3c, reflect at least a portion of light back to lens 14, admit the chemical substance to the region between lens 14 and reflector 20 but filter particulate from that region.

The foregoing description of preferred embodiments of the invention has been presented for purposes of illustration and description. It is not intended to be exhaustive or to limit the invention to the precise form disclosed, and obviously many modifications and variations are possible in light of the above teachings. The embodiments were chosen and described in order to best explain the principles of the invention and its practical application to thereby enable one skilled in the art to best utilize the invention in various embodiments and with various modifications as are suited to the particular use contemplated. It is intended that the scope of the invention be defined by the claims appended hereto.

What is claimed is:

1. A method for performing spectrophotometric measurements of an analyte in situ comprising the steps of:
    transmitting light from a remote light source through a first light transmitting means to a position proximate to said analyte;
    collimating said transmitted light with a planoconvex lens, said convex side toward said first light transmitting means;
    absorbing analyte onto an optically transparent substrate located proximate to said planoconvex lens and lying in the path of said collimated light;
    reflecting said collimated light from a porous, reflective material positioned in spaced relation to said planoconvex lens, said analyte therebetween;
    focusing said reflected light onto a second light transmitting means with said planoconvex lens, said convex side toward said second light transmitting means; and
    moving said material toward said first light transmitting means until said second light transmitting means receives sufficient light for said measurements.

* * * * *